United States Patent [19]

Seckinger et al.

[11] 4,248,621
[45] Feb. 3, 1981

[54] 1-METHYL-3-FORMYL-3-SUBSTITUTED UREAS

[75] Inventors: Karl Seckinger, Riegel, Fed. Rep. of Germany; Rudolf Sandmeier, Basel, Switzerland

[73] Assignee: Sandoz Ltd., Basel, Switzerland

[21] Appl. No.: 82,773

[22] Filed: Oct. 9, 1979

Related U.S. Application Data

[63] Continuation-in-part of Ser. No. 883,011, Mar. 3, 1978, abandoned, which is a continuation-in-part of Ser. No. 852,819, Nov. 18, 1977, abandoned, which is a continuation of Ser. No. 718,851, Aug. 30, 1976, abandoned.

[30] Foreign Application Priority Data

Sep. 5, 1975 [CH] Switzerland ................. 11591/75
Jul. 20, 1976 [GB] United Kingdom ............. 30117/76

[51] Int. Cl.³ .................... A01N 47/30; C07C 127/00
[52] U.S. Cl. ............................ 71/120; 260/453 RW; 564/45
[58] Field of Search ................ 71/120; 260/553 E

[56] References Cited

U.S. PATENT DOCUMENTS

| | | | |
|---|---|---|---|
| 2,762,695 | 9/1956 | Gerjovich et al. | 260/553 E |
| 2,876,088 | 3/1959 | Hill | 71/120 |
| 3,705,028 | 12/1972 | Janiak et al. | 260/553 E |
| 3,728,386 | 4/1973 | Maravetz | 71/120 X |
| 3,951,641 | 4/1976 | Janiak | 71/120 |

FOREIGN PATENT DOCUMENTS 2080809 1/1972 France .
1407586 9/1975 United Kingdom .
1407587 9/1975 United Kingdom .

*Primary Examiner*—Joseph Paul Brust
*Attorney, Agent, or Firm*—Gerald D. Sharkin; Richard E. Vila

[57] ABSTRACT

The present invention relates to the novel selective herbicidal use of certain phenyl ureas falling under the formula

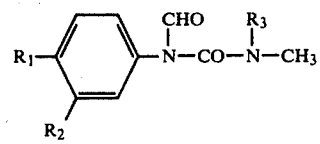

wherein
$R_1$ and $R_2$ are each, independently,
H, or substituents such as alkyl and
$R_3$ is H, methyl or methoxy, in cultivated crops.

24 Claims, No Drawings

1-METHYL-3-FORMYL-3-SUBSTITUTED UREAS

This application is a continuation-in-part of application Ser. No. 883,011, filed Mar. 3, 1978, now abandoned, which is a continuation-in-part of now abandoned application Ser. No. 852,819, filed Nov. 18, 1977, which in turn is a continuation of now abandoned application Ser. No. 718,851, filed Aug. 30, 1976.

The present invention relates to the herbicidal use of phenyl ureas.

Accordingly, the present invention provides a method of selectively combating weeds in a cultivated plant locus which comprises applying thereto a selective herbicidally effective amount of a compound of formula I

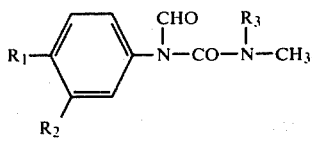

wherein
$R_1$ and $R_2$ are each, independently,
H, $(C_1-C_4)$ alkyl, $(C_1-C_4)$ alkoxy, trfluoromethyl, F, Cl or Br and
$R_3$ is H, methyl or methoxy with the provisos that
(a) when $R_3$ is H or methyl no more than one of $R_1$ and $R_2$ is H or no more than one of $R_1$ and $R_2$ is Cl or no more than one of $R_1$ and $R_2$ is a carbon containing group and
(b) when $R_3$ is H and
either $R_2$ is methyl and $R_1$ is H
or $R_2$ is Cl and $R_1$ is methyl
or when $R_3$ is methyl and
$R_2$ is H and $R_1$ is Cl or F
or $R_2$ is Cl and $R_1$ is H or methyl
or $R_2$ is H and $R_1$ is tert.butyl, then the cultivated crop is a cereal crop.

The compounds of formula Ia

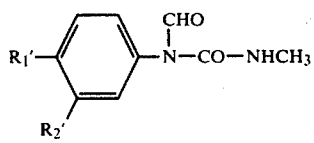

wherein
$R_1'$ and $R_2'$ are each independently, H, $(C_1-C_4)$alkyl, $(C_1-C_4)$alkoxy, trifluoromethyl, F, Cl or Br with the provisos that
(a) no more than one of $R_1'$ and $R_2'$ is H or no more than one of $R_1'$ and $R_2'$ is Cl or no more than one of $R_1'$ and $R_2'$ is a carbon containing group
(b) when $R_2'$ is methyl, $R_1'$ is other than H and when $R_2'$ is Cl, $R_1'$ is other than methyl,
the compounds of formula Ib

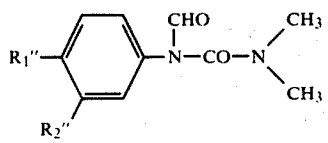

wherein
$R_1''$ and $R_2''$ are each, independently, H, $(C_1-C_4)$alkyl, $(C_1-C_4)$alkoxy, trifluoromethyl F, Cl or Br with the provisos that
(a) no more than one of $R_1''$ and $R_2''$ is H or no more than one of $R_1''$ and $R_2''$ is Cl or no more than one of $R_1''$ and $R_2''$ is a carbon containing group
(b) when $R_2''$ is H, $R_1''$ is other than Cl or F
(c) when $R_1''$ is methyl, $R_2''$ is other than Cl and
(d) when $R_1''$ is tert.-butyl $R_2''$ is other than H, and the compounds of formula Ic

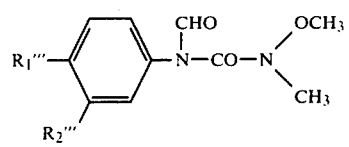

wherein
$R_1'''$ and $R_2'''$ are each, independently,
H, $(C_1-C_4)$alkyl, $(C_1-C_4)$alkoxy, trifluoromethyl, F, Cl or Br are new and also form part of the present invention.

The compounds of formula I wherein $R_3$ is hydrogen may be produced by condensing a compound of formula II

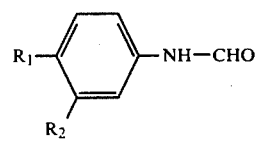

wherein
$R_1$ and $R_2$ are as defined above, with a compound of formula III $$CH_3NCO \qquad \qquad III$$

the process, insofar as it relates to the production of compounds of formula Ia also forming part of the present invention.

The compounds of formula I wherein $R_3$ is methyl or methoxy may be produced by condensing a compound of formula II, in sodium or potassium salt form, with a compound of formula IV

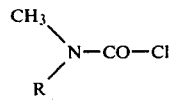

wherein R is methyl or methoxy, the process, insofar as it relates to the production of compounds of formulae Ib and Ic also forming part of the present invention.

Both reactions may be effected for example in an organic solvent such as a hydrocarbon, e.g. toluene, preferably under anhydrous conditions, at a temperature in the range 15° to 100° C.

The compounds of formula I possess a wide spectrum of herbicidal activity against both monocotyl and dicotyl weed species, e.g. *Alopecurus spp, Amaranthus retroflexus, Capsella bursa pastoris, Chenopodium album, Stellaria media, Senecio vulgaris, Echinochloa crus-galli, Poa annua, Agrostis alba, Sida spinosa, Setaria geniculata, Digitaria sanguinelis, Sisymbrium irio* and *Cyperia ro-* tunda. Moreover, at the dosage levels necessary to control the weeds, the compounds of formulae Ia, Ib and Ic cause no substantial damage in cultivated crops such as cereals especially barley and wheat, particularly the latter, rice, maize, sugar-cane, cotton, leguminous crops, ground nuts, soya, alfalfa, sugar beet, carrots, potato and flax, and the compounds of formula I other than the compounds of formulae Ia, Ib and Ic in cereals such as barley and wheat, particularly wheat and especially winter varieties.

It should be mentioned that certain of the compounds of formula I show a certain varietal dependency in their selective action in wheat. Thus, for example, the compound 1,1-dimethyl-3-formyl-3-(3-chloro-4-methylphenyl)-urea is not as well tolerated in wheat varieties such as Zenith, Heine VII, Tapro, Marella and Remois as in the varieties Probus, Capelle, Maris, Settler and Splendeur. Nevertheless, the degree of susceptibility of any variety in connection with any compound may be readily determined by simple greenhouse tests.

For the above-mentioned uses, the amount of compound to be applied to the cultivated crop will naturally vary depending on the particular crop, the compound employed, the mode of application, ambient conditions and the weed species to be treated. However, in general, satisfactory results are obtained when the compound is applied in the dosage range 0.5 to 5 kg/hectare, preferably 1 to 3.5 kg/hectare.

The compounds may be employed as herbicidal compositions in association with herbicide carriers or diluents. Such compositions also form part of the present invention.

Herbicidal compositions may be employed in either solid or liquid application forms. Solid forms, e.g. dusting forms and granulates, may be produced by mixing or impregnating solid herbicide carriers such as diatomaceous earth, kaolin, talc, chalk, limestone and cellulose powder, with the compounds.

Additives may be employed in the herbicidal composition. Typical of such additives are wetting and dispersing agents, e.g. the condensation product of formaldehyde with naphthalene sulphonate, and alkyl benzene sulphonates, adhesion imparting agents, e.g. dextrin, and emulsion stabilizers, e.g. ammonium caseinate. Such additives are suitable for incorporation into, e.g. a wettable powder form of composition or together with suitable solvents, e.g. hydrocarbons such as benzene, toluene, xylene, tetrahydronaphthalene, alkylated naphthalenes, kerosene, aromatic petroleum hydrocarbon fractions (e.g. commercial product Shellsol AB having b.pt. range 187°–213° C.) ketones such as isophorone, acetone, cyclohexanone, diisobutylketone and methylethylketone, alcohols such as isopropanol, ethanol, and methylcyclohexanol, chlorinated hydrocarbons such as tetrachloroethylene, ethylene chloride or trichloroethylene, to form emulsion concentrates.

The herbicidal compositions may contain, aside from a compound of formula I as active agent, other active agents, such as herbicides, e.g. of the urea class, halogen benzonitriles, carbamates and triazines.

Concentrate forms of composition generally contain between 2 and 80%, preferably between 2 and 50%, by weight of a compound of formula I as active agent.

Application forms of composition generally contain between 0.01 and 10%, by weight of a compound of formula I as active agent.

Specific Examples of herbicidal compositions will now be described.

EXAMPLE A

Wettable Powder 25 parts of a compound of formula I, e.g. 1,1-dimethyl-3-formyl-3-(4-tert.butylphenyl)-urea 1-methyl-3-formyl-3-(3-chloro-4-isopropylphenyl)-urea or 1-methyl-3-formyl-3-(4-isopropylphenyl) urea, 5 parts of a condensation product from formaldehyde and naphthalene sulphonate, 2 parts of alkyl benzene sulphonate, 5 parts of dextrin, 1 part of ammonium caseinate and 62 parts of diatomaceous earth are mixed until a homogeneous mixture is obtained and then ground until the particles are considerably smaller than 45 microns as an average.

EXAMPLE B

Emulsion Concentrate 25 parts of a compound of formula I, e.g. 1,1-dimethyl-3-formyl-3-(3-chloro-4-methylphenyl)-urea, 1,1-dimethyl-3-formyl-3-(3-chloro-4-isopropylphenyl) urea or 1-methyl-3-formyl-3-(3-trifluoromethylphenyl)urea, 65 parts of xylene and 10 parts of the mixed reaction product of an alkylphenol with ethylene oxide and calciumdodecylbenzene sulphonate are thoroughly mixed until a homogeneous solution is obtained. The resulting emulsion concentrate is diluted with water before use.

EXAMPLE C

Granulate 5 kg of a compound of formula I, e.g. 1,1-dimethyl-3-formyl-3-(3-trifluoromethylphenyl)-urea, 1-methyl-3-formyl-3-(3-chloro-4-isopropylphenyl) urea or 1-methyl-3-formyl-3-(4-isopropylphenyl)urea are dissolved in 25 l methylene chloride. The solution is then added to 95 kg of granulated attapulgate (mesh size 24/48 mesh/inch) and thoroughly mixed. The solvent is then evaporated off under reduced pressure with warming.

The application of the compounds may be either pre- or post-emergence of either the weeds or crop. Preferably the compounds are applied pre- or post-emergence of the crop particularly pre-emergence, in conventional manner.

The method of the present invention is preferably directed to the selective herbicidal use of the compounds of formula Id

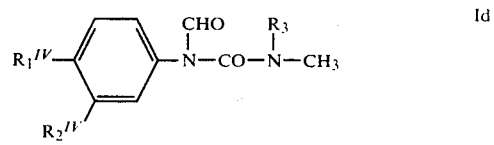

wherein
$R_1^{IV}$ is (C$_1$–C$_4$)alkyl or alkoxy
$R_2^{IV}$ is H or Cl and
$R_3$ is as defined above, with the proviso that when $R_1^{IV}$ is alkoxy, $R_2^{IV}$ is chlorine, in cereal crops, especially in wheat, particularly when $R_1^{IV}$ is isopropyl or isopropoxy and more particularly when $R_3$ is hydrogen or methyl.

The preferred novel compounds of the invention are the compounds of formula Iaa

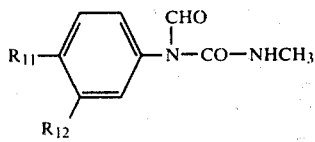

wherein $R_{11}$ is $(C_1-C_4)$ alkyl, especially $(C_2-C_3)$ alkyl, e.g. isopropyl, or $(C_1-C_4)$alkoxy and $R_{12}$ is H or Cl, with the provisos that when $R_{11}$ is methyl, $R_{12}$ is hydrogen and that when $R_{11}$ is alkoxy, $R_{12}$ is chlorine, and the compounds of formula Ibb

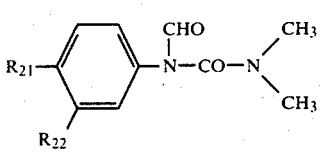

wherein $R_{21}$ is $(C_1-C_4)$ alkyl, especially $(C_2-C_3)$ alkyl, e.g. isopropyl or $(C_1-C_4)$ alkoxy, and $R_{22}$ is H or Cl with the provisos that when $R_{21}$ is methyl $R_{22}$ is H, and when $R_{21}$ is tert.butyl or alkoxy $R_{22}$ is chlorine.

The invention is further illustrated by the following Examples. Where temperature is referred to, this is in °C. and where percentages and parts are referred to, these are by weight.

EXAMPLE 1

1,1-Dimethyl-3-formyl-3-(4-isopropyl-phenyl)-urea

To a well stirred suspension of 2.4 g (0.1 Mol) sodium hydride in 150 ml absolute toluene is added at room temperature 15.5 g (0.095 Mol) 4-isopropylformanilide in 100 ml absolute toluene and the reaction mixture stirred for 20 hours at room temperature. To the resulting sodium salt suspension is added dropwise a solution of 10.8 g (0.1 Mol) dimethylcarbamoylchloride in 50 ml absolute toluene and the mixture finally heated for 10 minutes at 80°. After cooling to room temperature, the reaction mixture is filtered, the solvent evaporated off under vacuum and the residue dried under high vacuum at 40°/0.05 mm. The remaining viscous oil is dissolved in absolute ether to form a 60% solution, the solution left for 20 hours at −20° during which time the product crystallises out, is filtered off, washed with petroleum ether and recrystallised from its own weight of absolute alcohol. M.pt. 30°–32°. If, however, no crystals form on standing, the product is chromatographically purified on a neutral silica gel column using a chloroform/acetone (19:1) eluant mixture.

In analogous manner to the procedure described in the preceding Example, the compounds in Table 1 below are produced.

TABLE I

| Ex. No. | $R_1$ | $R_2$ | $R_3$ | M.Pt. °C./ Rf value* |
|---|---|---|---|---|
| 2 | H | $C_2H_5O$ | $CH_3$ | 74–76° |
| 3 | H | $i-C_3H_7O$ | $CH_3$ | 43–45° |
| 4 | H | sec. $C_4H_9O$ | $CH_3$ | Rf:0.69 |
| 5 | $C_2H_5O$ | H | $CH_3$ | 46° |

TABLE I-continued

| Ex. No. | $R_1$ | $R_2$ | $R_3$ | M.Pt. °C./ Rf value* |
|---|---|---|---|---|
| 6 | $i-C_3H_7O$ | H | $CH_3$ | 24–25° |
| 7 | sec. $C_4H_9O$ | H | $CH_3$ | Rf:0.64 |
| 8 | $CH_3O$ | Cl | $CH_3$ | 74–76° |
| 9 | $C_2H_5O$ | Cl | $CH_3$ | Rf:0.57 |
| 10 | $i-C_3H_7O$ | Cl | $CH_3$ | Rf:0.67 |
| 11 | Cl | $i-C_3H_7O$ | $CH_3$ | 77–78° |
| 12 | H | $CF_3$ | $CH_3$ | Rf:0.49 |
| 13 | Br | H | $CH_3$ | Rf:0.61 |
| 14 | Br | H | $CH_3O$ | 64–65° |
| 15 | H | $CH_3$ | $CH_3$ | Rf:0.30 |
| 16 | H | $C_2H_5$ | $CH_3$ | Rf:0.41 |
| 17 | H | $i-C_3H_7$ | $CH_3$ | Rf:0.33 |
| 17a | Cl | Cl | $CH_3O$ | Rf:0.22 |
| 18 | Cl | $CH_3$ | $CH_3$ | 65–66° |
| 19 | Br | $CH_3$ | $CH_3$ | 59–61° |
| 20 | Cl | $C_2H_5$ | $CH_3$ | Rf:0.31 |
| 21 | Cl | $i-C_3H_7$ | $CH_3$ | Rf:0.33 |
| 22 | $CH_3$ | H | $CH_3$ | Rf:0.32 |
| 23 | $C_2H_5$ | H | $CH_3$ | Rf:0.32 |
| 24 | $i-C_3H_7$ | H | $CH_3$ | 30–32° |
| 25 | sec. $C_4H_9$ | H | $CH_3$ | Rf:0.34 |
| 26 | tert. $C_4H_9$ | H | $CH_3$ | 117–119° |
| 27 | $CH_3$ | Cl | $CH_3$ | 49–51° |
| 28 | $C_2H_5$ | Cl | $CH_3$ | Rf:0.36 |
| 29 | $i-C_3H_7$ | Cl | $CH_3$ | 56–58° |
| 30 | $i-C_3H_7$ | Br | $CH_3$ | 64–65° |
| 31 | sec. $C_4H_9$ | Cl | $CH_3$ | 50–52° |
| 32 | tert. $C_4H_9$ | Cl | $CH_3$ | Rf:0.38 |
| 33 | F | H | $CH_3$ | 32–34° |

*silica gel - chloroform/acetone eluant (9:1)

EXAMPLE 34

1-Methyl-3-formyl-3-(3-methylphenyl)-urea

To a solution of 0.1 Mol of 3-methyl-formanilide in 150 ml absolute toluene are added 11.4 g (0.2 Mol) methylisocyanate and 1,5 ml triethylamine and the mixture container sealed and left to stand for 4–7 days at room temperature. The resulting precipitate is filtered off, washed with petroleum ether and dried to yield the title compound, m.pt. 112°–3°.

In analogous manner, the compounds of formula I wherein $R_3$ is H, set out in Table II below are obtained. If no precipitate is formed after 7 days, the solvent and excess methylisocyanate is evaporated off under vacuum, the product dried under high vacuum and recrystallised.

TABLE II

| Ex. No. | $R_2$ | $R_1$ | M.Pt. (recrystallisation solvent) |
|---|---|---|---|
| 35 | $i-C_3H_7$ | H | 61–3° (ether/petroleum ether) |
| 36 | H | $C_2H_5$ | 77–8° (ether/petroleum ether) |
| 37 | H | $i-3H_7$ | 130–1°* |
| 38 | H | $8-C_{C4H9}$ | 89–91° (ether/petroleum ether) |
| 39 | H | tert-$C_4H_9$ | 135–6°* |
| 40 | $CH_3$ | Cl | 108–110° (ether) |
| 41 | $CH_3$ | Br | 115–117° (ethanol) |
| 42 | Cl | $OCH_3$ | 141–143°* |
| 43 | Cl | $OC_2H_5$ | 106–108° (ethanol) |
| 44 | Cl | $O-iC_3H_7$ | 104–106° (ethanol) |
| 45 | F | H | 112–113°* |
| 46 | H | F | 160–161°* |
| 47 | $CF_3$ | H | oil Rf value 0.25** |
| 48 | H | Cl | 122–127°* |
| 49 | $i-C_3H_7$ | Cl | 84–5° |

TABLE II-continued

| Ex. No. | R₂ | R₁ | M.Pt. (recrystallisation solvent) |
|---|---|---|---|
| 50 | Cl | CH₃ | (ether/petroleum ether) 90-92° |
| 51 | Cl | C₂H₅ | (ether) 65-67° |
| 52 | Cl | i-C₃H₇ | (ether/petroleum ether) 99-101 |
| 53 | Cl | sec C₄H₉ | (ether) oil Rf value 0.4** |
| 54 | Cl | tert C₄H₉ | 112-4° (ether) |
| 55 | Br | i-C₃H₇ | 110-112° (ethanol) |
| 56 | OC₂H₅ | H | 105-109°* |
| 57 | H | Br | 145-6°* |
| 58 | Cl | H | 69-71° (ethanol) |
| 59 | H | CF₃ | 122-3° (ether) |
| 60 | Br | H | 76-7° (ethanol) |

N.B. *Crystallised directly from reaction mixture.
**silica gel - chloroform/acetone eluant (9:1)

EXAMPLE 61

Selective weed control—Pre-emergence treatment

Seed dishes are filled to a depth of 6 cm with a mixture of peat culture substrate No. 1 (obtainable from Torfstreuverband G.m.b.h, 29 Oldenberg, W. Germany) and sand. The exposed surface of the peat culture and sand mixture is sprayed with 50 ml of an aqueous solution of a compound of formula I (formulated in accordance with Example B) and various seeds (see below) are sown in each dish. After sowing of the seeds, the treated surface is covered with a thin layer (0.5 cm) of peat culture/sand mixture. The dishes are kept for 28 days at room temperature with 14 to 17 hours light per day.

Each of the compounds of Examples 1-3, 5, 7-10 and 12-60 (including 17a) are applied in the above manner at dosages corresponding to 1.5 kg/ha and 2.5 kg/ha.

The various plant species employed are *Alopecurus spp*, *Amaranthus retroflexus*, *Capsella bursa pastoris*, *Chemopodium album*, *Stellaria media*, *Senecio vulgaris*, *Echinochloa crus-galli*, *Poa annua*, *Agrostis alba*, *Triticum vulgare* (wheat-variety Probus), Hordium (barley), *Glycine soja* (soya), *Linum usitatissium* (flax), *Solanum tuberosum* (potato) and *Gossypium hirsutum* (cotton). In every case, herbicidal selectivity is observed, that is to say, significant damage to the weeds without substantial damage to the cultivated plants.

EXAMPLE 62

Selective weed control—Post-emergence treatment

A procedure similar to that employed in Example 61 is followed with the exception that the herbicide is applied when the plants are at the 2-4 leaf stage, the sowing of the plant seeds being staggered to ensure that the plants reach the 2-4 leaf stage at about the same time.

Again the compounds of Examples 1-3, 5, 7-10 and 12-60 (including 17a) are applied in the above manner at dosages corresponding to 1.5 kg/ha and 2.5 kg/ha.

The various plant species employed are *Chenopodium album*, *Stellaria media*, *Senecio vulgaris*, *Echinochloa crus-galli*, *Poa annua*, *Agrostis alba* and the cultivated crops listed in Example 61. In every case, herbicidal selectivity is observed.

In a particularly preferred aspect of the invention the compounds of Examples 29, 32, 52 and 54, hereinabove described, are particularly useful as selective herbicides in cereal crops, especially barley and wheat, whereby a good control of a broad spectrum of weeds, particularly broadleaf weeds, may be obtained at highly efficient low rates of application without substantial injury to the cereal crop. Such compounds may be applied for such use either pre-emergence or post emergence the crop, but are preferably applied post emergence such as, for example, at the early tillering stage in wheat. Application rates for such use of these preferred compounds in selectively combatting weeds in a cereal crop are from 0.5 to 3.5 kilograms per hectare, preferably from 0.8 to 2.5 kilograms per hectare. The more preferred compounds for use in cereals are those of Examples 52 and 54, hereinabove described, especially the compound of Example 52, and the use of current preferred interest involves the combatting of weeds in a wheat, particularly by application post-emergence the wheat, such as for example at the early tillering stage. Such interest and preference was confirmed, by way of illustration, in various field trials conducted in both summer and winter wheat in the western portion of the State of Washington employing an aqueous suspension of 50% wettable powder formulation of the active ingredient of Example 52 which is designated as SAN 315 in Table III, below, in which the application rates, dates of application and ratings as a percentage of damage for such trials are recorded. In Table III trials Nos. H 3047-147, H 3047-148 and H 3047-149 were conducted in summer wheat and trials Nos. H 3047-150 and H 3047-151 were conducted in winter wheat.

TABLE III

| | | | | % PHYTOTOXICITY | | | | | |
|---|---|---|---|---|---|---|---|---|---|
| TREATMENT | LB. AI/A | Trial No. Appl. Date Rate. Date | | H 3047-148 4/26/79 | | | H 3047-149 5/10/79 | H 3047-150 5/2/79 | H 3047-151 5/9/79 |
| | | | 4/30 | 5/8 | 5/16 | | 5/17 | 5/16 | 5/16 |
| SAN 315 | 0.9 | | 3 | 2 | 3 | | 5 | 8 | 0 |
| SAN 315 +X77 | 0.9 + 0.5% | | 32 | 22 | 22 | | 45 | 26 | 18 |
| SAN 315 | 1.8 | | 2 | 6 | 10 | | 5 | 5 | 0 |
| SAN 315 +X77 | 1.8 + 0.5% | | 58 | 53 | 55 | | 60 | 26 | 20 |

| | | % WEED CONTROL | | | | | | | | | | | | | |
|---|---|---|---|---|---|---|---|---|---|---|---|---|---|---|---|
| | | Trial No. | | | | | | | | | | | | | |
| | LB. | H 3047-148 | | | H 3047-149 | | | | | H 3047-150 | | | | H 3047-151 | |
| Treat- ment | AI/ A | | | | | | | | Weeds | | | | | | |
| | | GWC | LQ | KO | GWC | LQ | HE | PL | JM | GWC | ML | DF | HE | FID | GWC | JM | CHI | GWC |
| SAN 315 | 0.9 | 92 | 92 | 100 | 85 | 100 | 72 | 100 | 100 | 95 | 98 | 98 | 100 | 95 | 85 | 72 | 63 | 89 |

TABLE III-continued

| | | | | | | | | | | | | | | | | | | |
|---|---|---|---|---|---|---|---|---|---|---|---|---|---|---|---|---|---|---|
| SAN 315 + X77 | 0.9+ 0.5% | 93 | 95 | 97 | 93 | 100 | 98 | 100 | 100 | 93 | 95 | 100 | 98 | 100 | 77 | 78 | 78 | 89 |
| SAN 315 | 1.8 | 98 | 98 | 100 | 68 | 100 | 68 | 95 | 98 | 92 | 93 | 98 | 100 | 100 | 83 | 83 | 82 | 85 |
| SAN 315 + X77 | 1.8+ 0.5% | 100 | 100 | 100 | 97 | 100 | 97 | 100 | 100 | 97 | 97 | 100 | 100 | 100 | 80 | 85 | 82 | 94 |
| Check | — | 0 | 0 | 65 | 0 | 0 | 0 | 0 | 0 | 0 | 0 | 0 | 0 | 0 | 0 | 0 | 0 | 0 |

GWC = General Weed Control
LQ = Lambsquarter
KO = Ko hia
HE = Henbit
PL = Prickley lettuce
JM = Jim.Hill Mustard
ML = Miner lettuce
DF = Dog Fennel
FID = Fiddleneck
CHI = Chickweed In another particularly preferred aspect of the invention the compounds of Examples 29, 32, 52 and 54 are also indicated as particularly useful as selective herbicides in a soybean crop. Such compounds may be applied for such use either pre-emergence the crop or post-emergence, but desirably not beyond the 2-4 leaf stage. Application rates for such use of these preferred compounds in selectively combatting weeds in a soybean crop are from 0.5 to 3.5 kilograms per hectare, preferably from 0.8 to 2.5 kilograms per hectare. The more preferred compound for use in soybeans is that of Example 54 and the more desirable time of application is in the range of time from soil cracking by the emerging soybean plant to the end of the two leaf stage, more preferably at about the cracking stage or very soon thereafter.

In still another particularly preferred aspect of the invention the compounds of Examples 29, 32, 52 and 54 are also indicated as particularly useful as selective herbicides in peanuts (ground nuts). Such compounds may be applied for such use either pre-emergence or post-emergence the peanut crop, but are most effective when applied post emergence the peanut crop. Application rates for such use of these preferred compounds in selectively combatting weeds in a peanut crop are also from 0.5 to 3.5 kilogram per hectare, preferably from 0.8 to 2.5 kilograms per hectare. The more preferred compounds for such use are those of Examples 52 and 54, especially the compound of Example 54, and excellent results based on small plot screening trials in the United States are indicated for application at least in the time span from the dicotyledon stage to the 4 leaf stage.

An additional aspect of the invention indicated to be of particular interest involves the use of the compounds of Example 54 is the selective combatting of weeds in a corn crop by application post-emergence the corn, for example, when the corn is from 2 to 6 inches high, at rates preferably from 0.8 to 2.5 kilograms per hectare.

In a further particularly preferred embodiment of the invention the said compounds of Examples 29, 32, 52 and 54 are particularly useful in controlling weeds in perennial fruit and nut trees including but not limited to peach, apple, citrus, walnut, almond and pecan trees by direct spray to weed areas surrounding such existing trees at rates of from 0.6 to 3.5 kilograms per hectare, preferably 0.8 to 2.5 kilograms per hectare. The compounds of Examples 52 and 54 are also especially preferred for such control of weeds in fruit and nut trees, particularly the compound of Example 52.

A still further particularly preferred embodiment of the invention involves generally the use of the compounds of Examples 29, 32, 52 and 54 as so called burndown agents applied to combat weeds in areas where crops either do not exist or are by size or other factors tolerate to the herbicide in essentially any reasonable and practical amounts necessary to eradicate weeds. Such particular interest is based on the very high degree of herbicidal activity exhibited by such compounds and by the further observation that such high activity may be markedly increased by formulating or combining the compounds of the formula I with additives containing an acidic and/or acid buffering component. As shown in Table III, above, herbicidal activity was markedly increased in those applications containing the material designated X-77 which is an agricultural spreader obtained under the registered trademark ORTHO X-77 and which is composed of alkylarylpolyoxyethylene glycols, free fatty acids and isopropanol. In the trials in Table III the X-77 is used in an amount representing 0.5% by weight of the composition as diluted with water for spray application at the rate of 400 liters per acre. Another product with which similar results may be obtained is available from Colloidal Products Corporation (Sausalito, Calif.) under the designation Buffer X which contains 43.7% by weight of mono- and diorthophosphoric acid esters of nonylphenoxy polyoxyethylene glycol having 9-10 moles of ethylene oxide, 10.4% nonylphenoxy polyoxyethylene glycol having 9-10 moles of ethylene oxide, 2.9% of 85% phosphoric acid, 15.6% isopropanol, 25.6% water and 1.8% oleic acid. Such additives are also described in U.S. Pat. No. 3,244,502. Such acidic or acid buffering additives are typically used in an amount of from 0.1% to 3.0% based on the weight of the aqueous composition applied to the weeds, more usually in an amount of from 0.2% to 2.5%. As noted in Table III, the inclusion of the additive when having substantial spreading and sticking properties, while markedly enhancing herbicidal activity, may have in at least some cases an adverse effect upon selectively, and hence the addition of such additives is currently of main interest in burndown or general weed control applications.

What is claimed is:

1. A compound of the formula:

$$R_1\text{-}\underset{Cl}{\underset{|}{C_6H_3}}\text{-}\underset{\underset{CHO}{|}}{N}\text{-}CO\text{-}\underset{\underset{CH_3}{|}}{N}\text{-}R_3$$

wherein
$R_1$ is isopropyl or t-butyl, and
$R_3$ is hydrogen or methyl.

2. The compound of claim 1 in which $R_1$ is isopropyl and $R_3$ is hydrogen.

3. The compound of claim 1 in which $R_1$ is t-butyl and $R_3$ is hydrogen.

4. The method of combatting weeds comprising applying to a weed locus a herbicidally effective amount of a compound of claim 1.

5. The method of claim 4 in which the compound is the compound in which $R_1$ is isopropyl and $R_3$ is hydrogen.

6. The method of claim 4 in which the compound is the compound in which $R_1$ is t-butyl and $R_3$ is hydrogen.

7. The method of claim 4 of selectively combatting weeds in a cultivated locus of a crop which is wheat, barley, rice, maize, sugar cane, ground nut, soya, alfalfa, sugar beet, carrot, potato or flax comprising applying to such a locus an amount of the compound effective to combat weeds without substantially damaging the crop.

8. The method of claim 7 in which the crop is a wheat or barley crop.

9. The method of claim 8 in which the cereal is wheat.

10. The method of claim 8 in which the crop is a barley crop.

11. The method of claim 7 in which the crop is a soya crop.

12. The method of claim 7 in which the crop is a rice crop.

13. The method of claim 7 in which the crop is a maize crop.

14. The method of claim 7 in which the crop is a ground nut crop.

15. The method of claim 7, 8, 9, 10 or 11 in which the compound is the compound in which $R_1$ is isopropyl and $R_3$ is hydrogen.

16. The method of claim 7, 8, 9, 10 or 11 in which the compound is the compound in which $R_1$ is t-butyl and $R_3$ is hydrogen.

17. The method of claim 15 in which the compound is applied at a rate of from 0.5 to 5.0 kilograms per hectare.

18. The method of claim 17 in which the rate is from 1.0 to 3.5 kilograms per hectare.

19. The method of claim 16 in which the compound is applied at a rate of from 0.5 to 5.0 kilograms per hectare.

20. The method of claim 19 in which the rate is from 1.0 to 3.5 kilograms per hectare.

21. The method of claim 18 in which the compound is applied post-emergence the crop.

22. The method of claim 18 in which the compound is applied pre-emergence the crop.

23. The method of claim 20 in which the compound is applied post-emergence the crop.

24. The method of claim 20 in which the compound is applied pre-emergence the crop.

* * * * *